US010339649B2

(12) United States Patent
Ye et al.

(10) Patent No.: US 10,339,649 B2
(45) Date of Patent: Jul. 2, 2019

(54) METHOD AND SYSTEM FOR HYBRID MESH SEGMENTATION

(71) Applicant: Carestream Dental Technology Topco Limited, London (GB)

(72) Inventors: Wei Ye, Shanghai (CN); Shoupu Chen, Rochester, NY (US); Xavier Ripoche, Mandres les Roses (FR); Delphine Reynard, Montreuil (FR)

(73) Assignee: Carestream Dental Technology Topco Limited, London (GB)

( * ) Notice: Subject to any disclaimer, the term of this patent is extended or adjusted under 35 U.S.C. 154(b) by 0 days.

(21) Appl. No.: 14/851,332

(22) Filed: Sep. 11, 2015

(65) Prior Publication Data

US 2017/0076443 A1 Mar. 16, 2017

(51) Int. Cl.
| A61B 5/00 | (2006.01) |
|---|---|
| A61C 7/00 | (2006.01) |
| G06T 7/00 | (2017.01) |
| G06T 7/12 | (2017.01) |
| G06T 17/20 | (2006.01) |
| G06T 7/155 | (2017.01) |
| G06F 3/0482 | (2013.01) |

(Continued)

(52) U.S. Cl.
CPC .......... *G06T 7/0012* (2013.01); *A61B 5/0084* (2013.01); *A61B 5/0088* (2013.01); *A61B 5/4547* (2013.01); *A61B 5/7271* (2013.01); *A61B 5/742* (2013.01); *A61C 7/002* (2013.01); *G06F 3/0482* (2013.01); *G06F 3/04847* (2013.01); *G06T 7/12* (2017.01); *G06T 7/155* (2017.01); *G06T 17/20* (2013.01); *A61C 2007/004* (2013.01); *G06T 2200/04* (2013.01); *G06T 2207/20152* (2013.01); *G06T 2207/30036* (2013.01); *G06T 2207/30041* (2013.01)

(58) Field of Classification Search
None
See application file for complete search history.

(56) References Cited

U.S. PATENT DOCUMENTS

| 6,227,850 B1 * | 5/2001 | Chishti | .................... | A61C 7/00 |
| | | | | 433/213 |
| 6,409,504 B1 * | 6/2002 | Jones | ...................... | A61C 7/00 |
| | | | | 433/213 |

(Continued)

FOREIGN PATENT DOCUMENTS

WO     WO 00/19935     4/2000

OTHER PUBLICATIONS

Kumar et al., "Improved Segmentation of Teeth in Dental Models", Computer-Aided Design and Applications, 8(2), pp. 211-224.*

(Continued)

*Primary Examiner* — Matthew C Bella
*Assistant Examiner* — Jose Torres

(57) ABSTRACT

A computer-implemented method for generating a digital model of an individual intraoral component from a digital model of a patient's dentition obtains a 3-D digital mesh model of the patient's dentition and performs automatic tooth component segmentation operation on the obtained mesh model. Automated segmentation results display. Interactive segmentation of the automated segmentation results is performed according to an operator instruction. Segmentation results are displayed and stored.

15 Claims, 11 Drawing Sheets

(51) Int. Cl.
*G06F 3/0484* (2013.01)
*G06K 9/00* (2006.01)

(56) References Cited

U.S. PATENT DOCUMENTS

| | | | |
|---|---|---|---|
| 7,112,065 B2* | 9/2006 | Kopelman | A61C 13/0004 |
| | | | 433/213 |
| 2002/0102009 A1* | 8/2002 | Jones | A61C 7/00 |
| | | | 382/100 |
| 2003/0039389 A1 | 2/2003 | Jones et al. | |
| 2008/0199829 A1* | 8/2008 | Paley | A61B 5/4547 |
| | | | 433/215 |
| 2009/0316966 A1* | 12/2009 | Marshall | A61B 6/5217 |
| | | | 382/128 |
| 2016/0004811 A1* | 1/2016 | Somasundaram | G06F 17/50 |
| | | | 703/11 |
| 2016/0256035 A1* | 9/2016 | Kopelman | A61B 1/00009 |

OTHER PUBLICATIONS

Joe Min Moon, Evaluation of Software Developed for Automated Segmentation of Digital Dental Models, Thesis submitted on Feb. 2012, 56 pages.
Thomas Kronfeld et al., Snake-Based Segmentation of Teeth from Virtual Dental Casts, Computer-Aided Design & Applications, 7(a), 2010, pp. 1-12.
D.L. Page et al., Perception-based 3D Triangle Mesh Segmentation Using Fast Marching Watersheds, Proc. Intl. Conference on Computer Vision and Pattern Recognition, vol. 11, pp. 27-32, Jun. 2003.
International Search Report dated Jan. 11, 2017 for International Application No. PCT/US2016/049397, 2 pages.

* cited by examiner

METHOD AND SYSTEM FOR HYBRID MESH SEGMENTATION

TECHNICAL FIELD

The disclosure relates generally to segmentation of elements that are represented by a three-dimensional mesh and more particularly to methods and apparatus for tooth segmentation in a contour image that has been obtained using reflectance imaging.

BACKGROUND

Three-dimensional (3-D) imaging and 3-D image processing are areas of growing interest to dental/orthodontic practitioners for computer-aided diagnosis and overall improved patient care. In the field of cephalometric analysis, 3-D imaging and 3-D image processing offer significant advantages in terms of flexibility, accuracy, and repeatability. 3-D cephalometric analysis overcomes some of the shortcomings associated with conventional methods of two-dimensional (2-D) cephalometric analysis, such as 2-D geometric errors of perspective projection, magnification, and head positioning in projection, for example. 3-D cephalometrics has been shown to yield objective data that is more accurate, since it is based on calculation rather than being largely dependent upon discrete measurements, as is the case with 2-D cephalometrics.

Early research using 3-D cephalometrics methods employed 3-D imaging and parametric analysis of maxillofacial anatomical structures using cone beam computed tomography (CBCT) of a patient's head. Using CBCT methods, a significant role of the 3-D cephalometric analysis was to define mathematical models of maxillary and mandibular arches for which the axes of inertia were calculated for each tooth or group of teeth. This, in turn, required the segmentation of individual teeth from the acquired CBCT head volume of a patient.

Conventionally, during an orthodontic treatment procedure, multiple 2-D X-ray cephalogram acquisitions are used to assess treatment progress. Conventional 3-D cephalometric analysis can also be used for this purpose, requiring multiple CBCT scans. However, both 2-D and 3-D radiographic imaging methods expose the patient to ionizing radiation. Reducing overall patient exposure to radiation is desirable, particularly for younger patients.

Optical intraoral scans, in general, produce contours of dentition objects and have been helpful in improving visualization of teeth, gums, and other intra-oral structures. Surface contour information can be particularly useful for assessment of tooth condition and has recognized value for various types of dental procedures, such as for restorative dentistry. This can provide a valuable tool to assist the dental practitioner in identifying various problems and in validating other measurements and observations related to the patient's teeth and supporting structures. Surface contour information can also be used to generate 3-D models of dentition components such as individual teeth; the position and orientation information related to individual teeth can then be used in assessing orthodontic treatment progress. With proper use of surface contour imaging, the need for multiple 2-D or 3-D X-ray acquisitions of a patient's dentition can be avoided.

A number of techniques have been developed for obtaining surface contour information from various types of objects in medical, industrial, and other applications. Optical 3-dimensional (3-D) measurement methods provide shape and spatial information using light directed onto a surface in various ways. Among types of imaging methods used for contour imaging are fringe projection devices. Fringe projection imaging uses patterned or structured light and camera/sensor triangulation to obtain surface contour information for structures of various types. Once the fringe projection images are processed, a point cloud can be generated. A mesh can then be formed from the point cloud or a plurality of point clouds, in order to reconstruct at least a planar approximation to the surface.

Mesh representation can be particularly useful for showing surface structure of teeth and gums and can be obtained using a handheld camera and without requiring harmful radiation levels. However, when using conventional image processing approaches, mesh representation has been found to lack some of the inherent versatility and utility that is available using cone-beam computed tomography (CBCT) or other techniques that expose the patient to radiation. One area in which mesh representation has yielded only disappointing results relates to segmentation. Segmentation allows the practitioner to identify and isolate the crown and other visible portions of the tooth from gums and related supporting structure. Conventional methods for segmentation of mesh images can often be inaccurate and may fail to distinguish tooth structure from supporting tissues.

Various approaches for addressing the segmentation problem for mesh images have been proposed, such as the following:

(i) A method described in the article "Snake-Based Segmentation of Teeth from Virtual Dental Casts" by Thomas Kronfeld et al. (in Computer-Aided Design & applications, 7(a), 2010) employs an active contour segmentation method that attempts to separate every tooth and gum surface in a single processing iteration. The approach that is described, however, is not a topology-independent method and can fail, particularly where there are missing teeth in the jaw mesh.

(ii) An article entitled "Perception-based 3D Triangle Mesh Segmentation Using Fast Marching Watershed" by Page, D. L. et al. (in *Proc. CVPI* vol II 2003) describes using a Fast Marching Watershed method for mesh segmentation. The Fast Marching Watershed method that is described requires the user to manually enter seed points. The seed points must be placed at both sides of the contours of the regions under segmentation. The method then attempts to segment all regions in one step, using seed information. For jaw mesh segmentation, this type of method segments each tooth as well as the gum at the same time. This makes the method less desirable, because segmenting teeth from the gum region typically requires parameters and processing that differ from those needed for the task of segmenting teeth from each other. Using different segmentation strategies for different types of dentition components with alternate segmentation requirements would provide better performance.

(iii) For support of his thesis, "Evaluation of software developed for automated segmentation of digital dental models", J. M. Moon used a software tool that decomposed the segmentation process into two steps: separation of teeth from gingival structure and segmentation of whole arch structure into individual tooth objects. The software tool used in Moon's thesis finds maximum curvature in the mesh and requires the user to manually choose a curvature threshold to obtain margin vertices that are used for segmenting the tooth. The software also requires the user to manually edit margins in order to remove erroneous segmentation results. Directed to analysis of shape and positional characteristics, this software tool does not consider employing color information in the separation of teeth regions from the gum regions.

(iv) U.S. Patent application 20030039389 A1 entitled "Manipulation a digital dentition model to form models of individual dentition components" by Jones, T. N. et al. disclose a method of separating portions of the dentition model representing the adjacent teeth.

While conventional methods exhibit some level of success with a limited set of test cases, none of these methods appears to be robust and commercially viable. There is, then, a need for improved methods for segmentation of mesh representation of tooth and gum structures.

SUMMARY

An aspect of this application is to advance the art of tooth segmentation in relation to volume imaging and visualization used in medical and dental applications.

Another aspect of this application is to address, in whole or in part, at least the foregoing and other deficiencies in the related art.

It is another aspect of this application to provide, in whole or in part, at least the advantages described herein.

Method and/or apparatus embodiments according to the present disclosure can address particular needs for improved visualization and assessment of tooth position, wherein internal structures obtained using CBCT and other radiographic volume imaging methods can be correlated to reflectance image data obtained from the patient.

These objects are given only by way of illustrative example, and such objects may be exemplary of one or more embodiments of the application. Other desirable objectives and advantages inherently achieved by exemplary method and/or apparatus embodiments may occur or become apparent to those skilled in the art. The invention is defined by the appended claims.

According to one aspect of the disclosure, there is provided a computer-implemented method for generating a digital model of an individual intraoral component from a digital model of a patient's dentition, the method can include obtaining a 3-D digital mesh model of the patient's dentition; performing automatic tooth component segmentation on the obtained mesh model and displaying automated segmentation results; performing interactive segmentation of the automated segmentation results according to an operator instruction; and displaying and storing segmentation results.

According to one aspect of the disclosure, there is provided a computer-implemented method for generating a digital model of an individual intraoral component from a digital model of a patient's dentition, the method can include generating a 3-D digital mesh model of the patient's dentition from a plurality of structured light images; performing automatic tooth component segmentation on the obtained mesh model and displaying automated segmentation results; displaying a plurality of operator controls configured to adjust tooth component segmentation adjacent the displayed automated segmentation results; accepting at least one operator instruction related to segmentation of the displayed automated segmentation results entered through one or more of the plurality of operator controls; performing interactive segmentation of the displayed automated segmentation results according to the at least one operator instruction; and displaying, transmitting or storing segmentation results.

BRIEF DESCRIPTION OF THE DRAWINGS

The foregoing and other objects, features, and advantages of the invention will be apparent from the following more particular description of the embodiments of the invention, as illustrated in the accompanying drawings. Elements of the drawings are not necessarily to scale relative to each other.

DETAILED DESCRIPTION OF EXEMPLARY EMBODIMENTS

Figure 1:
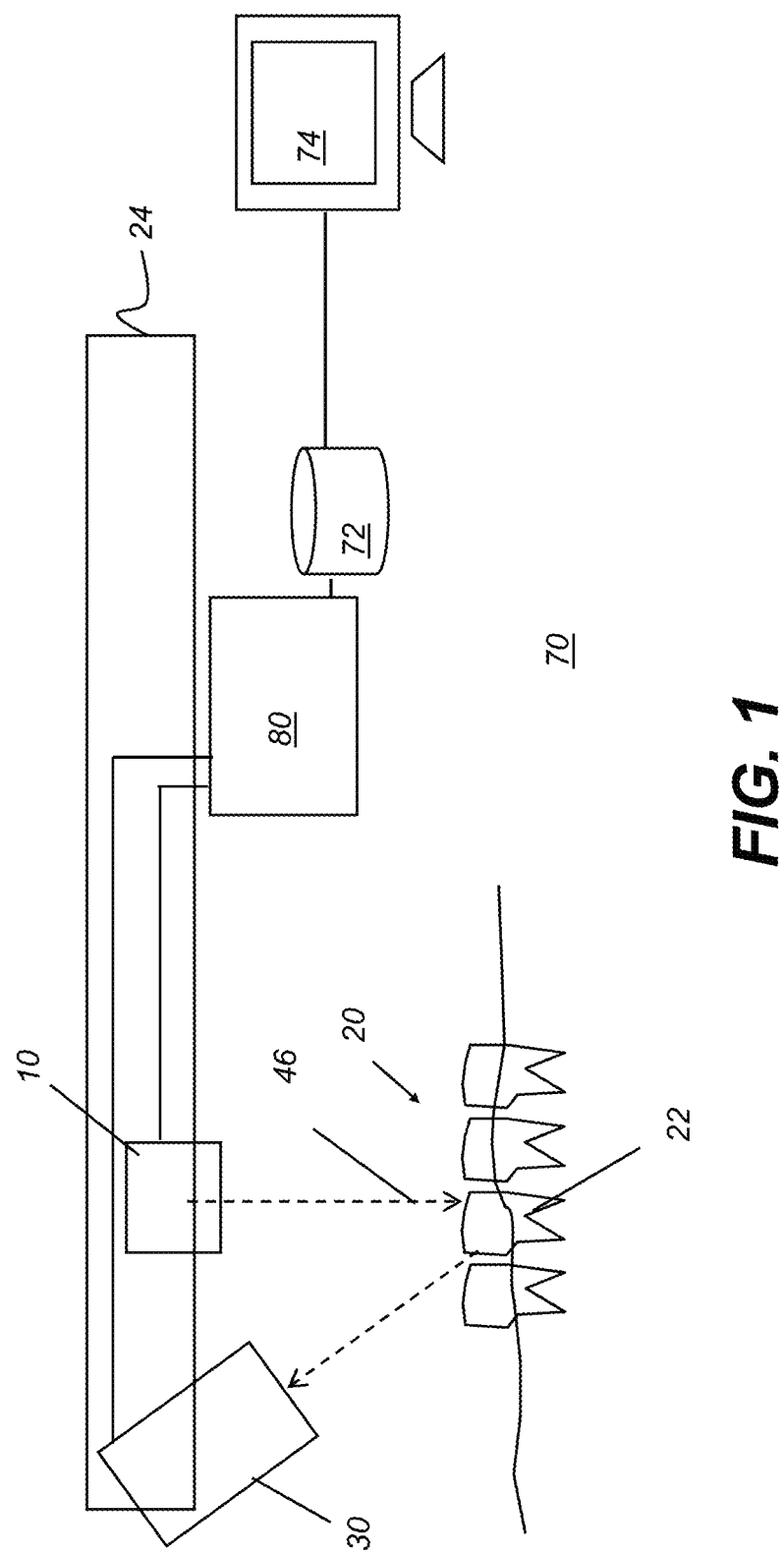
FIG. 1 is a schematic diagram that shows components of an imaging apparatus for surface contour imaging of a patient's teeth and related structures.

The following is a detailed description of exemplary embodiments, reference being made to the drawings in which the same reference numerals identify the same elements of structure in each of the several figures.

Where they are used, the terms "first", "second", and so on, do not necessarily denote any ordinal or priority relation, but may be used for more clearly distinguishing one element or time interval from another.

The term "exemplary" indicates that the description is used as an example, rather than implying that it is an ideal.

The term "in signal communication" as used in the application means that two or more devices and/or components are capable of communicating with each other via signals that travel over some type of signal path. Signal communication may be wired or wireless. The signals may be communication, power, data, or energy signals which may communicate information, power, and/or energy from a first device and/or component to a second device and/or component along a signal path between the first device and/or component and second device and/or component. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the context of the present disclosure, the terms "pixel" and "voxel" may be used interchangeably to describe an individual digital image data element, that is, a single value representing a measured image signal intensity. Conventionally an individual digital image data element is referred to as a voxel for 3-dimensional or volume images and a pixel for 2-dimensional (2-D) images. For the purposes of the description herein, the terms voxel and pixel can generally be considered equivalent, describing an image elemental datum that is capable of having a range of numerical values. Voxels and pixels have attributes of both spatial location and image data code value.

"Patterned light" is used to indicate light that has a predetermined spatial pattern, such that the light has one or more features such as one or more discernable parallel lines, curves, a grid or checkerboard pattern, or other features having areas of light separated by areas without illumination. In the context of the present disclosure, the phrases "patterned light" and "structured light" are considered to be equivalent, both used to identify the light that is projected onto the head of the patient in order to derive contour image data.

In the context of the present disclosure, the terms "viewer", "operator", and "user" are considered to be equivalent and refer to the viewing practitioner, technician, or other person who views and manipulates a contour image that is formed from a combination of multiple structured light images on a display monitor.

A "viewer instruction", "operator instruction", or "operator command" can be obtained from explicit commands entered by the viewer or may be implicitly obtained or derived based on some other user action, such as making an equipment setting, for example. With respect to entries entered on an operator interface, such as an interface using a display monitor and keyboard, for example, the terms "command" and "instruction" may be used interchangeably to refer to an operator entry.

In the context of the present disclosure, a single projected line of light is considered a "one dimensional" pattern, since the line has an almost negligible width, such as when projected from a line laser, and has a length that is its predominant dimension. Two or more of such lines projected side by side, either simultaneously or in a scanned arrangement, provide a two-dimensional pattern. IN exemplary embodiments, lines of light can be linear, curved or three-dimensional.

The terms "3-D model", "point cloud", "3-D surface", and "mesh" may be used synonymously in the context of the present disclosure. The dense point cloud is formed using techniques familiar to those skilled in the volume imaging arts for forming a point cloud and relates generally to methods that identify, from the point cloud, vertex points corresponding to surface features. The dense point cloud is thus generated using the reconstructed contour data from one or more reflectance images. Dense point cloud information serves as the basis for a polygon model at high density for the teeth and gum surface.

According to the present disclosure, the phrase "geometric primitive" refers to basic 2-D geometric shapes that can be entered by the operator in order to indicate areas of an image. By way of example, and not limitation, geometric primitives can include lines, curves, points, and other open shapes, as well as closed shapes that can be formed by the operator, such as circles, closed curves, rectangles and squares, polygons, and the like.

Embodiments of the present disclosure provide exemplary methods and/or apparatus that can help to eliminate the need for multiple CBCT scans for visualization of tooth and jaw structures. Exemplary methods and/or apparatus embodiments can be used to combine a single CBCT volume with optical intraoral scans that have the capability of tracking the root position at various stages of orthodontic treatment, for example. To achieve this, the intraoral scans are segmented so that exposed portions, such as individual tooth crowns, from the intraoral scan can be aligned with the individual tooth and root structure segmented from the CBCT volume.

FIG. 1 is a schematic diagram showing an imaging apparatus 70 for projecting and imaging using structured light patterns 46. Imaging apparatus 70 uses a handheld camera 24 for image acquisition according to an embodiment of the present disclosure. A control logic processor 80, or other type of computer that may be part of camera 24 controls the operation of an illumination array 10 that generates the structured light and controls operation of an imaging sensor array 30. Image data from surface 20, such as from a tooth 22, is obtained from imaging sensor array 30 and stored in a memory 72. Control logic processor 80, in signal communication with camera 24 components that acquire the image, processes the received image data and stores the mapping in memory 72. The resulting image from memory 72 is then optionally rendered and displayed on a display 74. Memory 72 may also include a display buffer for temporarily storing display 74 image content.

In fringe projection imaging of a surface, a pattern of lines is projected from illumination array 10 toward the surface of an object from a given angle. The projected pattern from the surface is then viewed from another angle as a contour image, taking advantage of triangulation in order to analyze surface information based on the appearance of contour lines. Phase shifting, in which the projected pattern is incrementally shifted spatially for obtaining additional measurements at the new locations, is typically applied as part of fringe projection imaging, used in order to complete the contour mapping of the surface and to increase overall resolution in the contour image.

Figure 2:
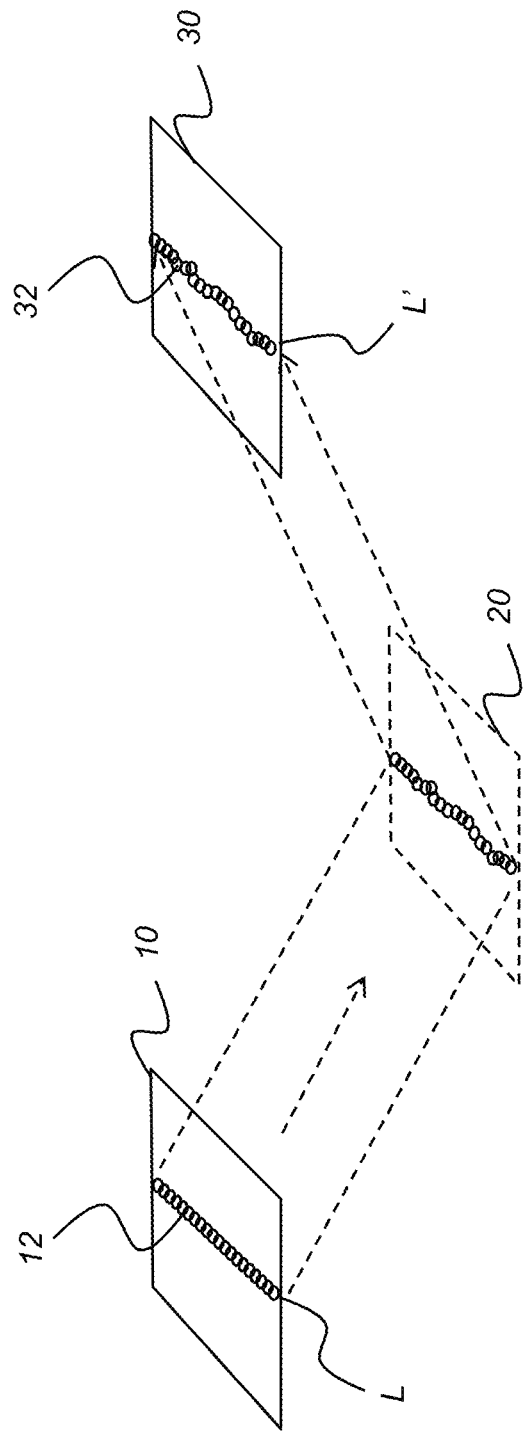
FIG. 2 shows schematically how patterned light is used for obtaining surface contour information using a handheld camera or other portable imaging device.

The schematic diagram of FIG. 2 shows, with the example of a single line of light L, how patterned light is used for obtaining surface contour information using a handheld camera or other portable imaging device. A mapping is obtained as an illumination array 10 directs a pattern of light onto a surface 20 and a corresponding image of a line L' is formed on an imaging sensor array 30. Each pixel 32 on imaging sensor array 30 maps to a corresponding pixel 12 on illumination array 10 according to modulation by surface 20. Shifts in pixel position, as represented in FIG. 2, yield useful information about the contour of surface 20. It can be appreciated that the basic pattern shown in FIG. 2 can be implemented in a number of ways, using a variety of illumination sources and sequences and using one or more different types of sensor arrays 30. Illumination array 10 can utilize any of a number of types of arrays used for light modulation, such as a liquid crystal array or digital micromirror array, such as that provided using the Digital Light Processor or DLP device from Texas Instruments, Dallas, Tex. This type of spatial light modulator is used in the illumination path to change the light pattern as needed for the mapping sequence.

By projecting and capturing images that show structured light patterns that duplicate the arrangement shown in FIGS. 1 and 2 multiple times, the image of the contour line on the camera simultaneously locates a number of surface points of the imaged object. This can speed the process of gathering many sample points, while the plane of light (and usually also the receiving camera) is laterally moved in order to "paint" some or all of the exterior surface of the object with the plane of light.

Figure 3:
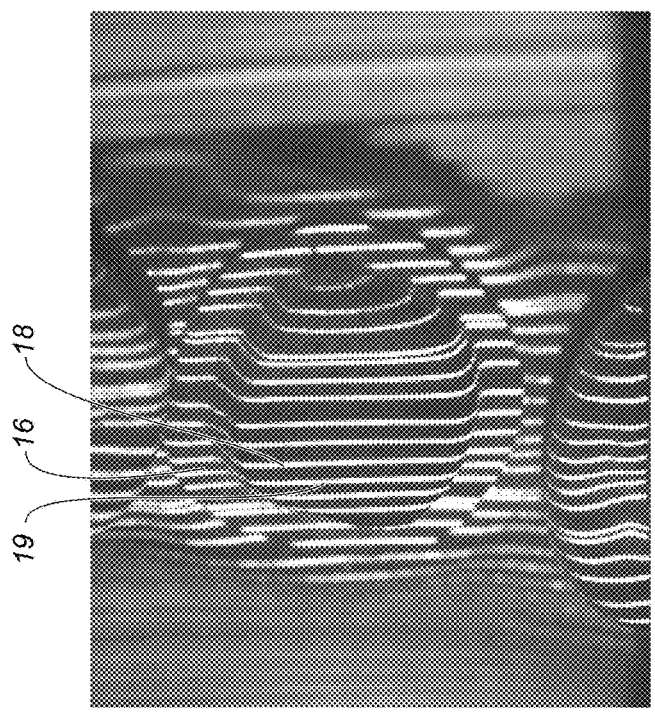
FIG. 3 shows an example of surface imaging using a pattern with multiple lines of light.

FIG. 3 shows surface imaging using a pattern with multiple lines of light. Incremental shifting of the line pattern and other techniques help to compensate for inaccuracies and confusion that can result from abrupt transitions along the surface, whereby it can be difficult to positively identify the segments that correspond to each projected line. In FIG. 3, for example, it can be difficult to determine whether line segment 16 is from the same line of illumination as line segment 18 or adjacent line segment 19.

Figure 4:
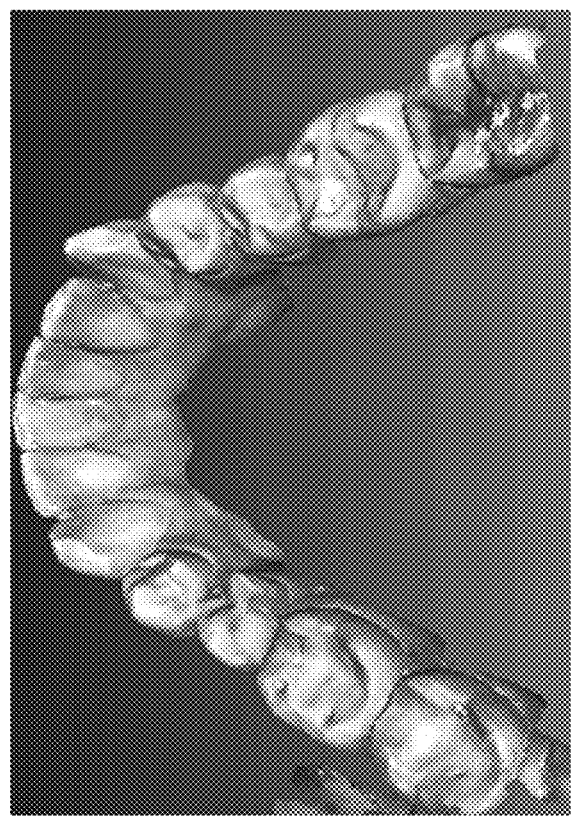
FIG. 4 shows a point cloud generated from structured light imaging, such as that shown in FIG. 3.

By knowing the instantaneous position of the camera and the instantaneous position of the line of light within an object-relative coordinate system when the image was acquired, a computer and software can use triangulation methods to compute the coordinates of numerous illuminated surface points. As the plane is moved to intersect eventually with some or all of the surface of the object, the coordinates of an increasing number of points are accumulated. As a result of this image acquisition, a point cloud of vertex points or vertices can be identified and used to represent the extent of a surface within a volume. By way of example, FIG. 4 shows a dense point cloud 50 generated from a structured light imaging apparatus, CS 3500 3-D camera made by Carestream Heath, Inc., Rochester N.Y., USA, using results from patterned illumination such as that shown in FIG. 3. The point cloud 50 models physical location of sampled points on tooth surfaces and other intraoral surfaces or, more generally, of surfaces of a real-world object. Variable resolution can be obtained. The example of FIG. 4 shows an exemplary 100 micron resolution. The points in the point cloud represent actual, measured points on the three dimensional surface of an object.

The surface structure can be approximated from the point cloud representation by forming a polygon mesh, in which adjacent vertices are connected by line segments. For a vertex, its adjacent vertices are those vertices closest to the vertex in terms of Euclidean distance.

Figure 5:
FIG. 5 shows a polygon mesh in the simple form of a triangular mesh.

By way of example, FIG. 5 shows a 3-D polygon mesh model 60 in the simple form of a triangular mesh. A triangular mesh forms a basic mesh structure that can be generated from a point cloud and used as a digital model to represent a 3-D object by its approximate surface shape, in the form of triangular plane segments sharing adjacent boundaries. Methods/apparatus for forming a polygon mesh model, such as a triangular mesh or more complex mesh structure, are well known to those skilled in the contour imaging arts. The polygon unit of the mesh model, and relationships between neighboring polygons, can be used in embodiments of the present disclosure to extract features (e.g., curvatures, minimum curvatures, edges, spatial relations, etc.) at the teeth boundaries.

In intra-oral imaging, segmentation of individual components of the image content from a digital model can be of value to the dental practitioner in various procedures, including orthodontic treatment and preparation of crowns, implants, and other prosthetic devices, for example. Various methods have been proposed and demonstrated for mesh-based segmentation of teeth from gums and of teeth from each other. However, drawbacks of conventional segmentation solutions include requirements for a significant level of operator skill and a high degree of computational complexity. Conventional approaches to the problem of segmenting tooth components and other dentition features have yielded disappointing results in many cases. Exemplary method and/or apparatus embodiments according to the present disclosure address such problems with segmentation that can utilize the polygonal mesh data as a type of source digital model and can operate in more than one stage: e.g., first, performing an automated segmentation algorithm/procedures that can provide at least a close or coarse approximation of the needed segmentation of the digital model; and second, allowing operator interactions to improve, correct and/or clean up observed errors and inconsistencies in the automated results, which can yield highly accurate results that are difficult to achieve in a purely automated manner, but not placing significant requirements on operator time or skill level and/or on needed computer resources. This hybrid approach in exemplary method and/or apparatus embodiments can help to combine computing and image processing power with operator perception to check, correct, and refine results of automated processing.

Figure 6A:
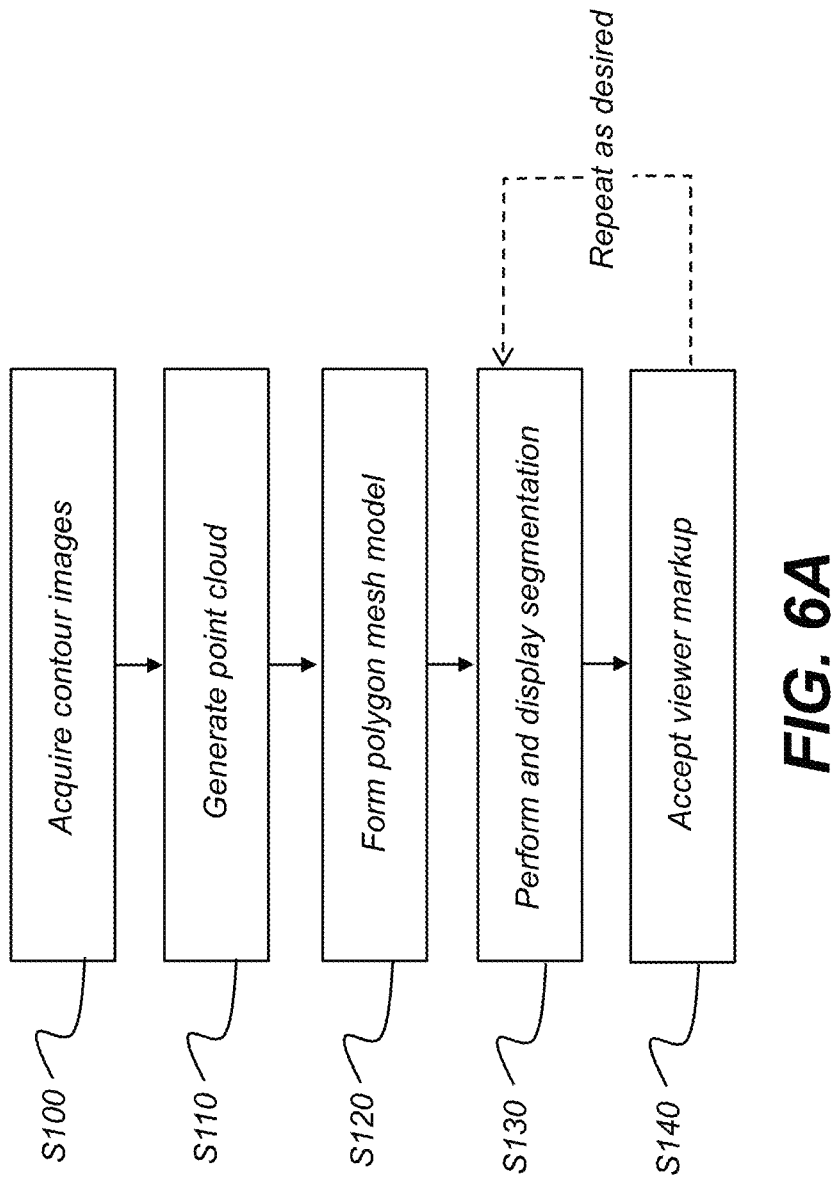
FIG. 6A is a logic flow diagram that shows a hybrid sequence for mesh segmentation according to an embodiment of the present disclosure.

The logic flow diagram of FIG. 6A shows a hybrid sequence for tooth mesh segmentation and generation of a digital model to identify individual features or intraoral components such as teeth from within the mouth according to an exemplary embodiment of the present disclosure. In an image acquisition step S100, a plurality of structured light images of the patient's dentition are captured, providing a set of contour images for processing. A point cloud generation step S110 then generates a point cloud of the patient's dentition using the set of contour images. A polygon mesh generation step S120 forms a polygon mesh by connecting adjacent points from the point cloud results. A triangular mesh provides one type of polygon mesh that can be readily generated for approximating a surface contour; more complex polygon mesh configurations can alternately be used.

Continuing with the FIG. 6A sequence, given the polygon mesh, a segmentation step S130 can be executed. For a dental contour image, for example, segmentation step S130 can distinguish teeth from gum tissue, as well as distinguishing one tooth from another. Segmentation results can then be displayed, showing the results of this initial, automated segmentation processing. The automated segmentation step S130 can provide an intermediate image. Thus automated step S130 can perform the bulk of segmentation processing, but can further benefit from operator review and refinements of results. For its automatic processing, segmentation step S130 can use any of a number of known segmentation techniques, such as fast-marching watershed algorithms, so-called snake-based segmentation, and other methods known to those skilled in the imaging arts, as noted earlier.

FIG. 6A also shows an optional repeat loop that can enable viewer interaction with the intermediate image for refining the results of the automated segmentation processing, for example, using the basic apparatus shown in FIG. 1. An accept operator instructions step S140 can be executed, during which the viewer indicates, on the displayed results, seed points, seed lines, block lines, boundary features, or other markings that identify one or more distinct features of the segmentation results to allow further segmentation refinement and processing. Viewer markup instructions cause segmentation step S130 to be executed at least a second time, this second time using input markup(s) from entered viewer instructions. It can be appreciated that different segmentation algorithms can be applied at various stages of automated or manual processing. Final results of segmentation processing can be displayed, stored, and transmitted between computers, such as over a wired or wireless network, for example.

The process shown in FIG. 6A can thus allow automated segmentation to perform the coarse segmentation (e.g., first segmentation) that can be more easily accomplished, such as segmentation of teeth from gum tissue, for example. Thus, for example, tooth and gum partitioning can be automated. In one embodiment, tooth and gum partitioning can use an automated curvature-based method that computes curvature of vertices in the mesh, and then uses a thresholding algorithm to identify margin vertices having large negative curvature. Alternately, color-based segmentation can be used for tooth segmentation from the gums. This type of method can obtain average hue values from regions of the image and calculate threshold values that partition image content.

Figure 6B:
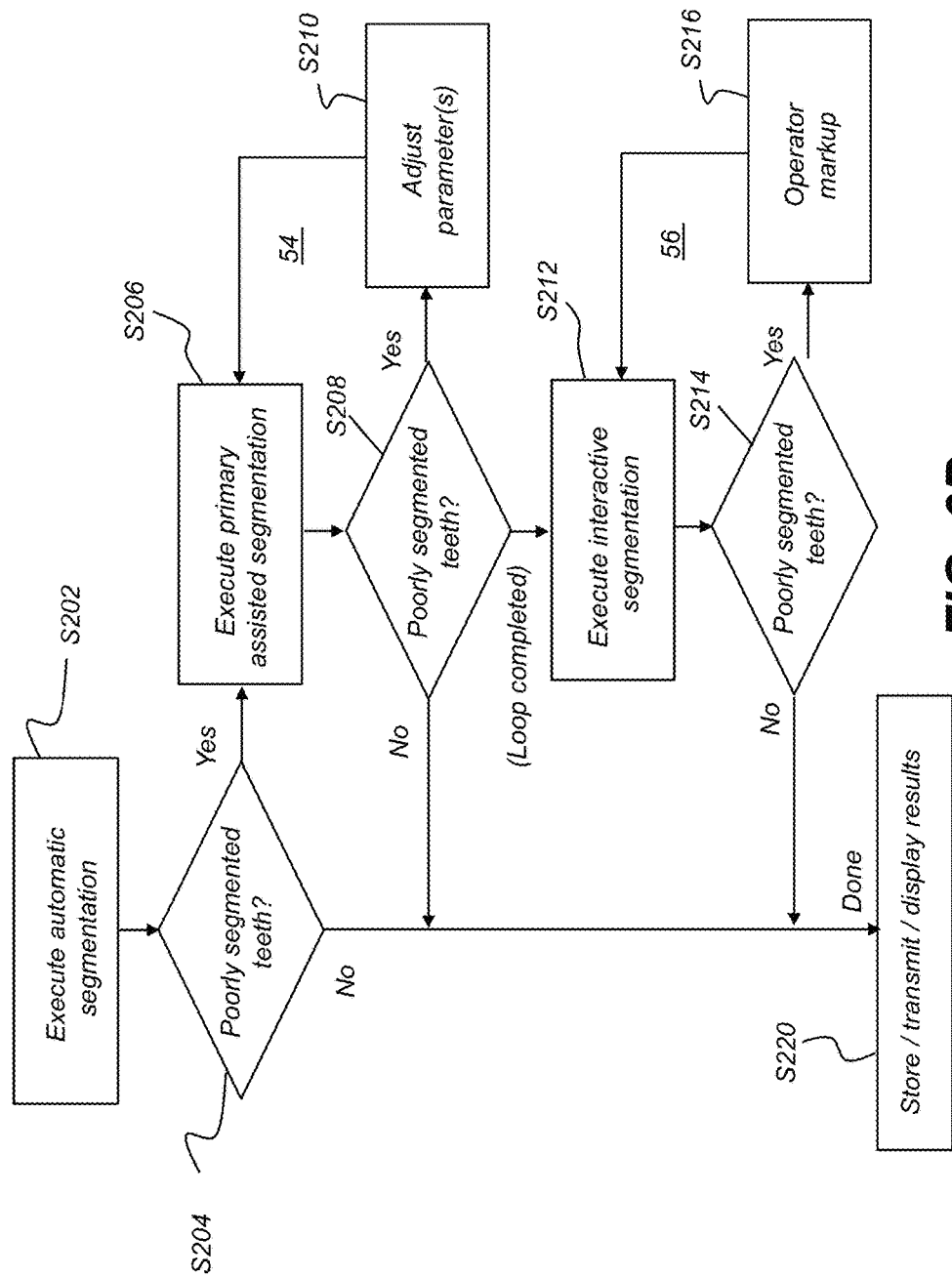
FIG. 6B is a logic flow diagram that shows a workflow sequence for hybrid segmentation of the tooth according to an embodiment of the present disclosure.
Figure 7B:
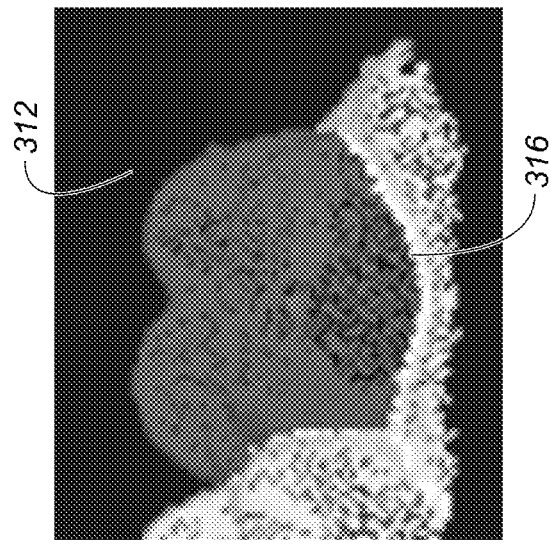
FIG. 7B shows an example of an improved segmentation.
Figure 7A:
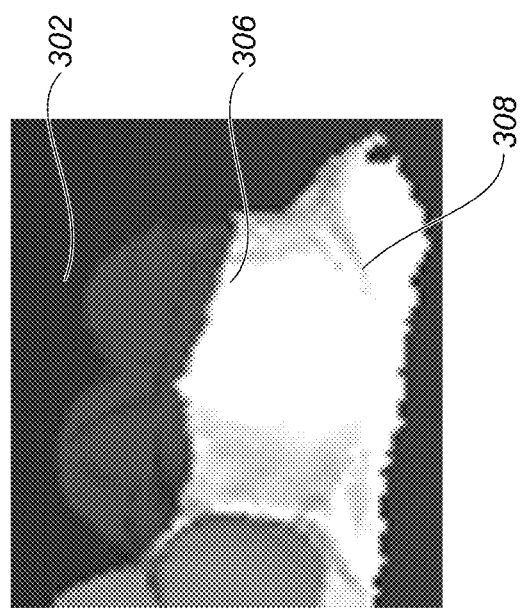
FIG. 7A shows an example of a poorly segmented tooth.

An exemplary embodiment of workflow for the hybrid tooth segmentation system is depicted in the logic flow diagram of FIG. 6B. Upon receiving a dentition mesh such as the one described in Step S120 and shown in FIGS. 4 and 5, the control logic processor 80 (FIG. 1) initiates an automated segmentation step S202 in which a fully automatic tooth segmentation tool is evoked to delineate teeth and gum regions and delineate individual teeth regions. The fully automatic tooth segmentation tool employs exemplary algorithms such as active contour models published in the literature or otherwise well-known to those skilled in the image processing arts. The delineation of teeth effectively produces individually segmented teeth; however, these generated teeth may contain poorly segmented intraoral components. A first checking step S204 then checks for poorly segmented intraoral components. Checking for incorrect or incomplete segmentation in step S204 can be accomplished either computationally, such as by applying trained artificial intelligence algorithms to the segmentation results, or by viewer interaction, such as following visual inspection by the viewer. By way of example, FIG. 7A shows an exemplary poorly segmented or mis-segmented tooth 302. As shown in FIG. 7A, a segmented tooth boundary 306 is not aligned with an actual tooth boundary 308.

Still referring to the workflow process in FIG. 6B, if checking Step S204 identifies one or more poorly segmented teeth, either computationally or visually, a primary assisted segmentation step S206 executes, activating a segmentation procedure that is also automated, but allows some level of operator adjustment. Primary assisted segmentation step S206 applies an algorithm for segmentation that allows operator adjustment of one or more parameters in a parameter adjustment step S210. Another checking step S208 executes to determine if additional segmentation processing is needed. The adjustable parameter can be altered computationally or explicitly by an operator instruction in step S210. Subsequent figures show an exemplary operator interface for parameter adjustment.

An exemplary algorithm employed in primary assisted segmentation Step S206 can be a well-known technique, such as the mesh minimum curvature-based segmentation method. The adjustable parameter can be the threshold value of the curvature. With the help of the parameter adjustment in step S210, a correction of the poorly segmented tooth can be made. FIG. 7B shows an image of tooth 312 that, by comparison with FIG. 7A, shows a segmented tooth boundary 316 now well aligned with the actual boundary.

Figure 8B:
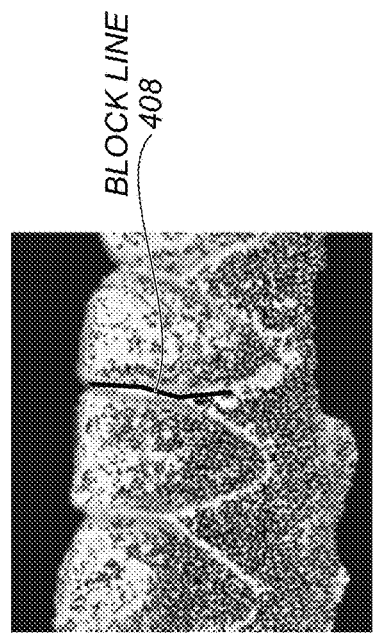
FIG. 8B shows an example of a block line trace pattern.
Figure 8A:
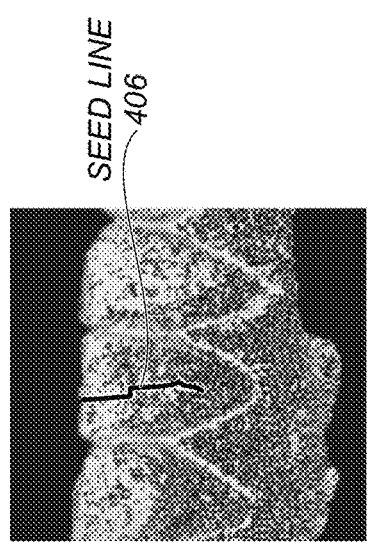
FIG. 8A shows an example of a seed line trace pattern.

However, as is clear from the exemplary workflow embodiment shown in FIG. 6B, the delineation of teeth performed in Step S206 may still produce poorly segmented intraoral components or features, so that a repeated segmentation process is helpful. The checking of poor segmentation in step S208 can be accomplished either computationally, such as by applying artificial intelligence algorithms to the segmentation results, or more directly, by visual inspection performed by the user. In addition to the adjustable parameter adjusted in Step S210, the hybrid tooth segmentation system optionally allows the user to add exemplary geometric primitives such as seed lines on the tooth region and add blocking lines between the teeth or between the teeth and gum to aid the tooth segmentation process. FIG. 8A shows an exemplary seed line 406 for marking a tooth, added to a mesh image 62. FIG. 8B shows an exemplary block line 408 for indicating space between two teeth, added to a mesh image 62.

The three basic steps, Step S206, Step S208 and Step S210 in the FIG. 6B sequence constitute an exemplary primary segmentation loop 54 that follows the fully automatic segmentation of step S202 and checking step S204. This exemplary primary segmentation loop 54 is intended to correct segmentation errors from the fully automated segmentation of automated segmentation step S202, as identified in step S204. Exemplary primary segmentation loop 54 can be executed one or more times, as needed. When exemplary primary segmentation loop 54 is successful, segmentation can be complete.

In some cases, however, additional segmentation processing beyond what is provided by primary segmentation loop 54 is needed. Segmentation processing can be complicated by various factors, such as tooth crowding, irregular tooth shapes, artifacts from scanning, indistinct tooth contours, and undistinguishable interstices among others. Where additional segmentation is needed, an exemplary secondary segmentation loop 56 can be used to provide more interactive segmentation approaches. The secondary segmentation loop 56 can include an interactive segmentation step S212, another checking step S214, and an operator markup step S216. Interactive segmentation step S212 can activate a segmentation process that works with the operator for indicating areas of the image to be segmented from other areas. Interactive segmentation step S212 can have an automated sequence, implemented by an exemplary algorithm such as a "fast march" method known to those skilled in the image segmentation arts. Step S212 may require population of the tooth region images by operator-entered seeds or seed lines or other types of geometric primitives before activation or during processing. In certain exemplary embodiments, seed lines or other features can be automatically generated in Step S100, S110 and S120 when the dentition mesh is entered into the system for optional operator adjustment (e.g., subsequent operations such as secondary segmentation loop 56 or Step 212). In addition, the features, seeds or seed lines can be added to the segmentation process in operator markup Step S216 by the user. The results from Step S212 are subject to inspection by the user in Step S216. Results from the hybrid automated/interactive segmentation processing can then be displayed in a display step S220, as well as stored and transmitted to another computer.

Following the sequence of FIG. 6B, some exemplary methods/apparatus of the present disclosure provide a hybrid tooth segmentation that provides the benefits of interactive segmentation with human-machine synergy.

Figure 9A:
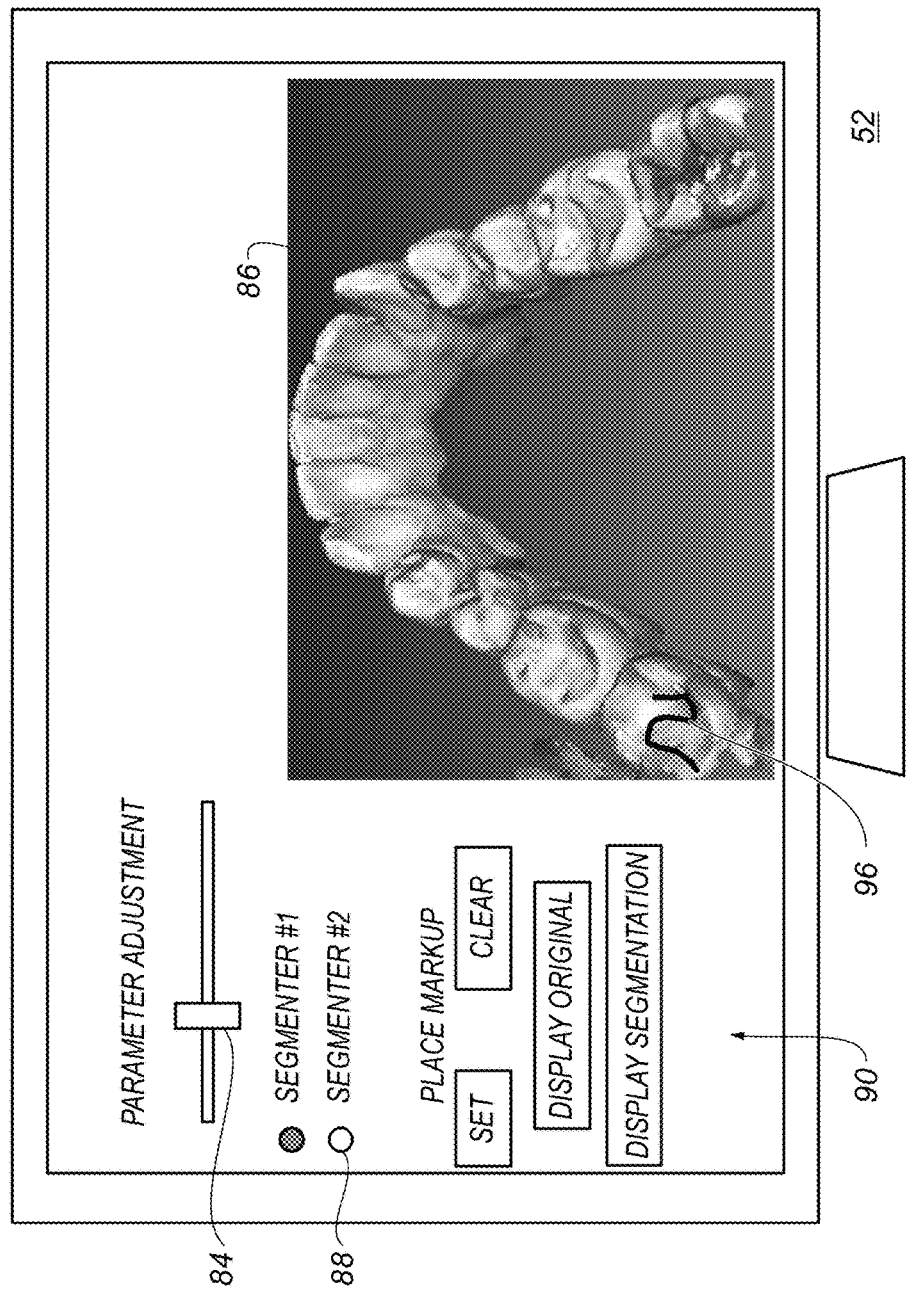
FIGS. 9A, 9B and 9C show operator interface screens for review and entry of markup instructions for refining tooth mesh segmentation processing according to certain embodiments of the present disclosure.
Figure 9B:
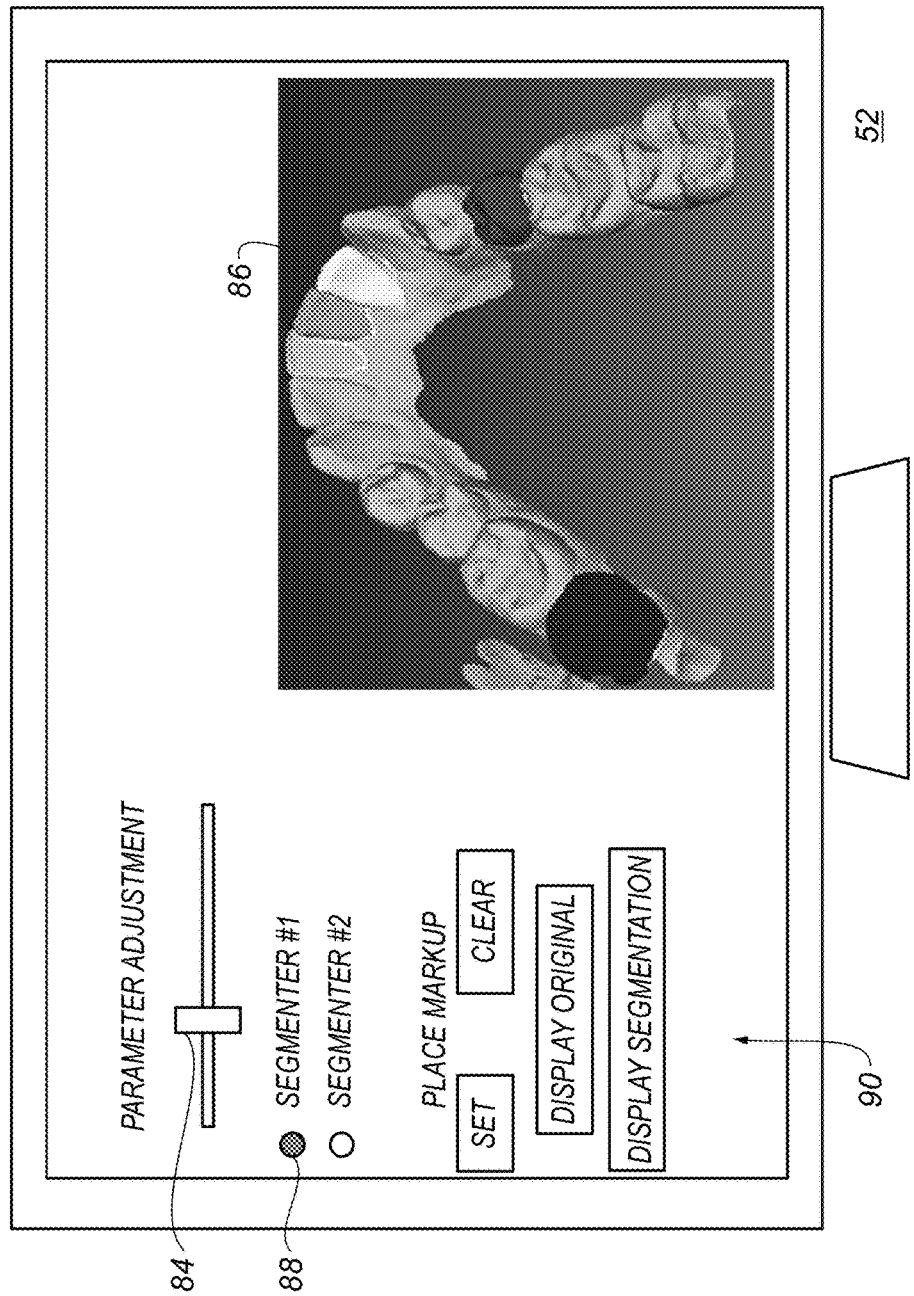
Figure 9C:
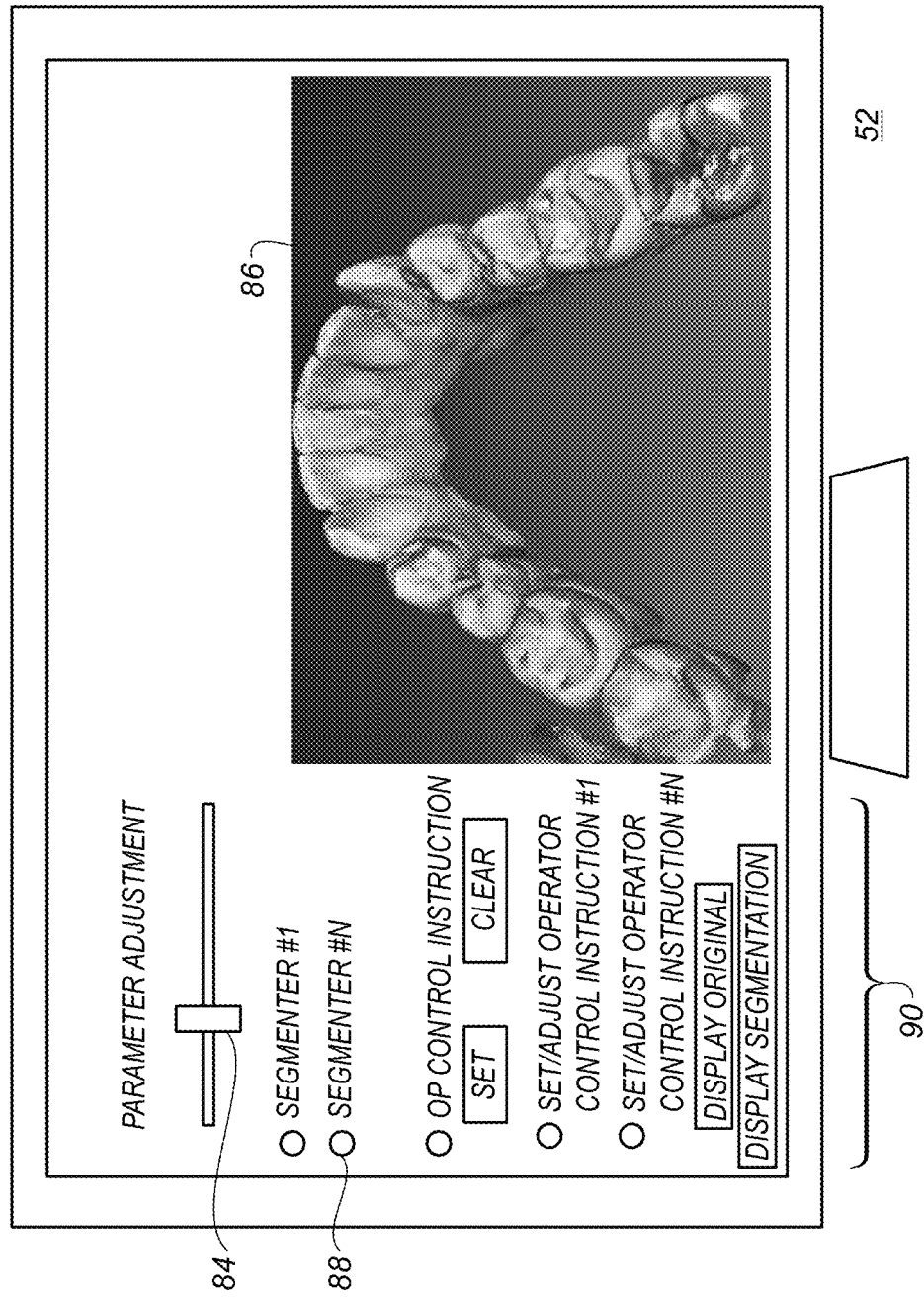

FIGS. 9A-9C show operator interface screens 52 for portions of a sequence for review and entry of markup instructions for refining mesh segmentation processing according to certain exemplary embodiments of the present disclosure. Interim mesh segmentation results are shown in a display area 86 on screen 52. A number of controls 90 for adjustment of the segmentation process are available, such as an adjustment control 84 for setting a level for overall aggressiveness or other parameter or characteristic of the segmentation processing algorithm. Optional selection controls 88 allow the viewer to specify one or more segmentation algorithms to be applied. This gives the operator an opportunity to assess whether one particular type of segmentation algorithm or another appear to be more successful in performing the segmentation task for the given mesh digital model. The operator can compare results against the original and adjust parameters to view results of successive segmentation attempts, with and without operator markup.

FIG. 9A also shows a trace pattern 96 that is entered as an operator seed line instruction for correcting or refining segmentation processing, as was shown previously with respect to FIG. 8A. According to an embodiment of the present disclosure, an operator mark in the form of trace pattern 96 or other arbitrary marking/geometric can be used to provide seed points that indicate a specific feature for segmentation, such as a molar or other tooth feature that may be difficult to process for conventional segmentation routines. Seed marks can then be used as input to a fast marching algorithm or other algorithm type, as described previously. In some cases, for example, adjacent teeth may not be accurately segmented with respect to each other; operator markup can provide useful guidance for segmentation processing where standard segmentation logic does not perform well. As FIG. 9A shows, the operator can have controls 90 available that allow the entered markup to be cleared or provided to the segmentation processor. As FIG. 9B shows, color or shading can be used to differentiate various teeth or other structures identified by segmentation. Additional controls 90 can also be used to display individual segmented elements, such as individual teeth, for example. As FIG. 9C highlights, in some exemplary embodiments, individual controls 90 can be used individually or in combination.

In one embodiment, segmentation of individual teeth from each other can use curvature thresholds to compute margin and border vertices, then use various growth techniques to define the bounds of each tooth relative to margin detection.

In some exemplary embodiments, controls 90 can include, but are not limited to enter/adjust seed or boundary geometrics, enter/adjust selected segmentation procedures, enter/adjust number of objects to segment, subdivide selected object, modify segmented object display, etc.

Consistent with one embodiment, the present disclosure can use a computer program with stored instructions that control system functions for image acquisition and image data processing for image data that is stored and accessed from an electronic memory. As can be appreciated by those skilled in the image processing arts, a computer program of an embodiment of the present invention can be utilized by a suitable, general-purpose computer system, such as a personal computer or workstation that acts as an image processor, when provided with a suitable software program so that the processor operates to acquire, process, transmit, store, and display data as described herein. Many other types of computer systems architectures can be used to execute the computer program of the present invention, including an arrangement of networked processors, for example.

The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other network or communication medium. Those skilled in the image data processing arts will further readily recognize that the equivalent of such a computer program product may also be constructed in hardware.

It is noted that the term "memory", equivalent to "computer-accessible memory" in the context of the present disclosure, can refer to any type of temporary or more enduring data storage workspace used for storing and operating upon image data and accessible to a computer system, including a database. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It is understood that the computer program product of the present disclosure may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim.

Exemplary embodiments according to the application can include various features described herein (individually or in combination).

While the invention has been illustrated with respect to one or more implementations, alterations and/or modifications can be made to the illustrated examples without departing from the spirit and scope of the appended claims. The presently disclosed embodiments are therefore considered in all respects to be illustrative and not restrictive. In addition, while a particular feature of the invention can have been disclosed with respect to one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims, and all changes that come within the meaning and range of equivalents thereof are intended to be embraced therein.

What is claimed is:

1. A computer-implemented method for generating a digital model of an individual intraoral component from a digital model of a patient's dentition, the method comprising:
obtaining a 3-D digital mesh model of the patient's dentition;
performing a first automatic tooth component segmentation on the obtained 3-D digital mesh model and displaying first automated tooth segmentation results;
performing a second interactive tooth segmentation on said displayed first automated tooth segmentation results according to an operator instruction to adjust a segmentation parameter of the first automatic tooth component segmentation method;
displaying and storing second tooth segmentation results that combine the first automatic tooth component segmentation and the second interactive tooth segmentation;
performing a third interactive tooth segmentation on said second tooth segmentation results according to at least one second operator instruction to select a different second type segmentation method and adjust a segmentation parameter of the different second type segmentation method;
displaying and storing third tooth segmentation results that combine the first automatic tooth component segmentation, the second interactive tooth segmentation, and the third interactive tooth segmentation;
accepting a third operator instruction to modify the displayed third segmentation results and then perform a fourth interactive tooth component segmentation using the modified third segmentation results; and
displaying and storing combined segmentation results that combine the first automatic tooth component segmentation, the second interactive tooth component segmentation, the third interactive tooth component segmentation, and the fourth interactive tooth component segmentation.

2. The method of claim 1 wherein the first automated tooth segmentation results distinguish one or more teeth from the patient's gum tissue.

3. The method of claim 1 wherein the first automated tooth segmentation results distinguish individual teeth from each other.

4. The method of claim 1 wherein the operator instruction identifies a tooth.

5. The method of claim 1 wherein the operator instruction verifies a tooth segmentation result.

6. The method of claim 1 wherein the operator instruction adds one or more geometric primitives to aid tooth segmentation.

7. The method of claim 1 wherein obtaining the 3-D mesh model comprises acquiring a plurality of structured light images from a hand-held intraoral camera.

8. The method of claim 1 wherein the results of first automated tooth segmentation appear in color.

9. The method of claim 1 wherein the first automated tooth segmentation employs a fast marching algorithm.

10. The method of claim 1 wherein the operator instruction comprises a traced line segment.

11. The method of claim 1 further comprising transmitting the combined segmentation results of interactive segmentation over a network to another computer.

12. A non-transitory computer-readable storage medium, storing program instructions computer-executable on a computer to perform operations comprising:
generating a 3-D digital mesh model of a patient's dentition;
performing first automatic tooth component segmentation on the obtained 3-D digital mesh model using a first type segmentation method and displaying automated tooth segmentation results, where the first automated tooth component segmentation initially distinguishes one or more teeth from the obtained 3-D digital mesh model;
accepting at least one operator instruction to to adjust a segmentation parameter of the first type segmentation method for the displayed automated tooth segmentation results;
performing second interactive tooth component segmentation of the displayed automated tooth segmentation results according to the at least one operator instruction;
displaying second tooth segmentation results that combine the first automatic tooth component segmentation and the second interactive tooth segmentation;
performing a third interactive tooth segmentation on said second tooth segmentation results according to at least one second operator instruction to select a different second type segmentation method and adjust a segmentation parameter of the different second type segmentation method;
displaying and storing third tooth segmentation results that combine the first automatic tooth component segmentation, the second interactive tooth segmentation, and the third interactive tooth segmentation;
accepting a third operator instruction to modify the displayed third segmentation results and then perform a fourth interactive tooth component segmentation using the modified third segmentation results;
displaying and storing combined segmentation results that combine the first automatic tooth component segmentation, the second interactive tooth component segmentation, the third interactive tooth component segmentation, and the fourth interactive tooth component segmentation.

13. The method of claim 12 wherein the at least one operator instruction identifies an error in the displayed automated tooth segmentation results.

14. The method of claim 12 wherein the 3-D digital mesh model is a triangular mesh.

15. An apparatus with machine implementable instructions configured to generate a digital model of an individual intraoral component from a digital model of a patient's dentition, comprising:

means for obtaining a 3-D digital mesh model of the patient's dentition;

means for performing first automatic tooth component segmentation using a first type segmentation method on the obtained 3-D digital mesh model and displaying automated tooth component segmentation results;

means for performing second interactive tooth component segmentation on the automated tooth component segmentation results according to an operator instruction to select a different second type segmentation method or to adjust a segmentation parameter of the first type segmentation method or the second type segmentation method;

means for displaying second tooth segmentation results that combine the automatic tooth component segmentation and interactive tooth component segmentation results;

means for performing a third interactive tooth segmentation on said second tooth segmentation results according to at least one second operator instruction to select a different second type segmentation method and adjust a segmentation parameter of the different second type segmentation method;

means for displaying and storing third tooth segmentation results that combine the first automatic tooth component segmentation, the second interactive tooth segmentation, and the third interactive tooth segmentation;

means for performing fourth interactive tooth component segmentation on the combined segmentation results according to an operator instruction to modify the displayed combined segmentation results and then perform a fourth interactive tooth component segmentation using the modified third segmentation results; and means for displaying segmentation results that combine the first automatic tooth component segmentation, the second interactive tooth component segmentation, the third interactive tooth component segmentation, and the fourth interactive segmentation results.

* * * * *